United States Patent [19]

Fuess

[11] Patent Number: Plant 6,920

[45] Date of Patent: Jul. 11, 1989

[54] CHRYSANTHEMUM PLANT NAMED PINK CHAMPAGNE

[76] Inventor: Janet S. Fuess, 9011 Red Hill Rd., New Hartford, N.Y. 13413

[21] Appl. No.: 141,251

[22] Filed: Jan. 6, 1988

[51] Int. Cl.[4] ..... A01H 5/00

[52] U.S. Cl. ..... Plt./76

[58] Field of Search ..... Plt./76

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Pink Champagne, characterized by its lavender pink ray floret color, almost fully double and shatter-resistant flowers, compact cushion habit, freely branching and flowering, seven week flower response, floriferousness, and its early natural flowering season in the garden.

1 Drawing Sheet

The present invention comprises a new and distinct cultivar of *Chrysanthemum morifolium,* Ramat., hereinafter referred to by the cultivar name Pink Champagne.

Pink Champagne is a product of a planned breeding program which had the objective of creating new Chrysanthemum cultivars with freely branching compact cushion habit, early flower response and large lavender decorative flowers, making it suitable for production as a garden variety. Such traits in combination were not present or needed improvement in previously available commercial cultivars.

Pink Champagne was originated from a hybridization made by applicant in a controlled breeding program in New Hartford, N.Y. in September 1985. The female parent was Debonaire, disclosed in U.S. Plant Pat. No. 5,324. The male parent of Pink Champagne was an unnamed seedling. Pink Champagne was discovered and selected as one flowering plant within the progeny of the stated parentage by applicant in August 1986 in a controlled environment in New Hartford, N.Y.

The first act of asexual reproduction of Pink Champagne was accomplished when vegetative cuttings were taken from the initial selection in March 1987 in a controlled environment in New Hartford, N.Y. by a technician working under formulations established and supervised by applicant. Horticultural examination of selected units initiated in Aug. 1987 has demonstrated that the combination of characteristics as herein disclosed for Pink Champagne are firmly fixed and are retained through successive generations of asexual reproduction.

The following traits have been repeatedly observed and are determined to be basic characteristics of Pink Champagne, which in combination distinguish this Chrysanthemum as a new and distinct cultivar:

1. Lavender pink ray floret color.
2. Almost fully double flowers, with only a few disc florets present.
3. Flowers very resistant to shattering.
4. Fully expanded ray florets approximately 30–35 mm long and 7–8 mm wide.
5. Average of 360 ray florets per capitulum.
6. Capitulum 6–8 cm in diameter.
7. Seven week flower response.
8. Performs well in the outdoor garden, flowering early in natural season.
9. Compact cushion habit, making it suitable for production in 4" to one gallon containers.
10. Freely branching and flowering.

Pink Champagne has not been observed under all possible environmental conditions. The phenotype may vary significantly with variations in environment such as temperature, light intensity, and day length. The following observations, measurements and comparisons describe plants grown in New Hartford, N.Y. under greenhouse conditions which approximate those generally used in commercial practice.

Of the many commercial cultivars known to the present inventor, the most similar in comparison to Pink Champagne is the maternal parent Debonaire. In comparison to Debonaire, Pink Champagne has a lighter pink flower color, much larger fower size, and a one week earlier flower response. The compact growth habit is similar to the same characteristic of Debonaire.

The accompaying photographic drawing shows typical inflorescence and foliage characteristics of Pink Champagne. The drawing is a black and white photograph with one flower showing the true color of Pink Champagne.

In the following description, color references are made to the Royal Horticultural Society Colour Chart. The color values were determined between 2:00–3:00 p.m. on Sept. 28, 1987 under fluorescent light at Parrish, Fla.

Classification:

*Botanical.*—*Chrysanthemum morifolium,* Ramat., c.v. Pink Champagne.

*Commercial.*—Decorative garden mum.

INFLORESCENCE

A. Capitulum:
- *Form.*—Flat.
- *Type.*—Double.
- *Diameter across face.*—6–8 cm.

B. Corolla of ray florets:
- *Color (general tonality from a distance of three meters).*—Lavender.
- *Color (upper surface).*—75A-B.
- *Color (under surface).*—75D.

C. Corolla of disc florets:
- *Color (mature).*—Yellow.
- *Color (immature).*—Yellow-green.

D. Reproductive organs:
- *Androecium.*—Very few; present in disc florets only.
- *Gynoecium.*—Present in both disc and ray florets.

PLANT

A. General appearance:

*Height.*—25–35 cm when grown in a 7½″ pot. Height can vary depending upon growing conditions, growth regulator applications and other cultural practices.

B. Foliage:

*Color (upper surface).*—147A.

*Color (under surface).*—147B.

*Shape.*—Ovate with cleft margins.

I claim:

1. A new and distinct cultivar of Chrysanthemum plant named Pink Champagne, as illustrated and described, and parts thereof.

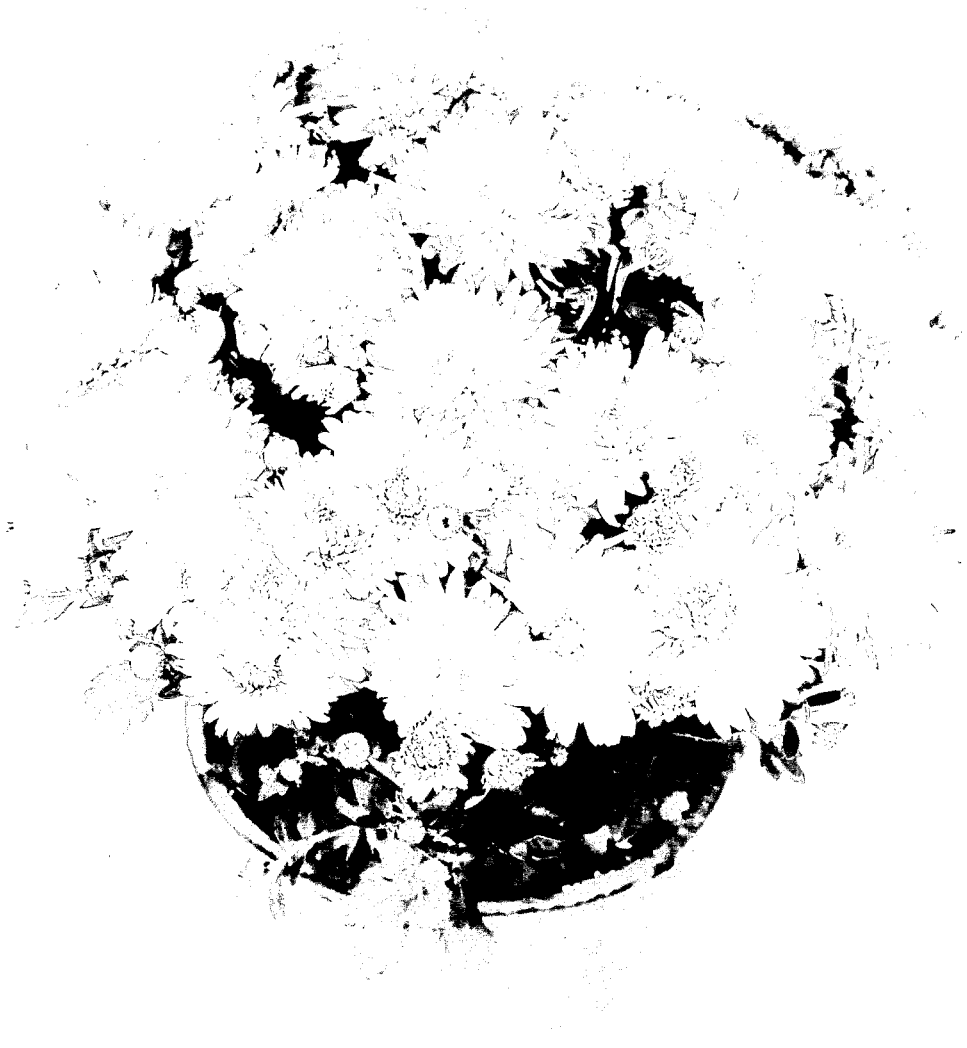

* * * * *